United States Patent [19]

Meier et al.

[11] Patent Number: 5,684,202
[45] Date of Patent: Nov. 4, 1997

[54] TERTIARY AMINES, A PROCESS FOR THEIR PREPARATION AND THEIR USE AS HARDENING ACCELERATORS

[75] Inventors: Helmut-Martin Meier, Ratingen; Wolfgang Fischer, Meerbusch; Horst Clemens, Krefeld, all of Germany

[73] Assignee: Bayer Aktiengesellschaft, Leverkusen, Germany

[21] Appl. No.: 523,995

[22] Filed: Sep. 5, 1995

[30] Foreign Application Priority Data

Sep. 14, 1994 [DE] Germany .................... 44 32 648.3

[51] Int. Cl.$^6$ .................................. C07C 211/53
[52] U.S. Cl. .................. 564/349; 525/326.1; 525/327.6; 525/329.5; 525/329.9; 525/379; 525/380; 525/437; 528/272; 528/274; 564/350
[58] Field of Search .................... 564/349, 350; 525/326.1, 327.6, 329.5, 329.9, 379, 380, 437; 528/272, 274

[56] References Cited

U.S. PATENT DOCUMENTS

| | | | |
|---|---|---|---|
| 3,785,832 | 1/1974 | Bowen | 106/35 |
| 4,243,763 | 1/1981 | Argentar | 525/27 |
| 4,284,551 | 8/1981 | Argentar | 260/42.43 |
| 4,297,158 | 10/1981 | Wolinski et al. | 156/305 |

FOREIGN PATENT DOCUMENTS

| | | |
|---|---|---|
| 625701 | 12/1961 | Belgium . |
| 84 784 | 8/1983 | European Pat. Off. . |
| 510265 | 10/1992 | European Pat. Off. . |
| 1544698 | 8/1970 | Germany . |
| 2120653 | 12/1983 | United Kingdom . |

*Primary Examiner*—Peter G. O'Sullivan
*Attorney, Agent, or Firm*—Joseph C. Gil; Richard E.L. Henderson

[57] ABSTRACT

The present invention relates to novel tertiary amines derived from bisphenoles, diepoxides and aromatic secondary amines, to a process for their preparation and to their use as hardening accelerators for ethylenically unsaturated cold hardenable acrylic and polyester resins.

4 Claims, No Drawings

TERTIARY AMINES, A PROCESS FOR THEIR PREPARATION AND THEIR USE AS HARDENING ACCELERATORS

BACKGROUND OF THE INVENTION

The present invention relates to novel N,N-disubstituted arylamines based on secondary aromatic amines and specific bisepoxides, a process for preparing such N,N-disubstituted arylamines, and their use as hardening accelerators for unsaturated acrylic and polyester resins, especially in cold hardening surface fillers.

According to European Patent Application 84,784, it is known that N,N-bis(β-hydroxyalkyl)arylamine derivatives can be used as hardening accelerators for surface fillers. According to Belgian Patent 625,701, it is known that aromatic amines with glycidyl terminal groups can be used to harden unsaturated polyester resins. According to British Patent 2,120,653, it is known that reaction products from primary amines and epoxides can be used as hardening accelerators. According to U.S. Pat. No. 4,243,763, it is known that tertiary amines derived from p-aminophenylacetic acid can be used as accelerators for peroxide-catalyzed polymerizations of unsaturated polyesters. According to U.S. Pat. No. 4,297,158, it is known that reaction products from N-methylaniline and epoxides can be used as accelerators for acrylates in polyurethane elastomer adhesives. However, N-ethyl-m-toluidine and N-ethyl-p-toluidine have not been used as starting materials. Use in surface fillers has not been described. According to U.S. Pat. No 4,284,551, it is known that tertiary aromatic amines derived from p-aminophenethanol can be used as accelerators for peroxide-catalyzed polymerizations of unsaturated polyester resins. According to German Offenlegungsschrift 1,544,698, di-tertiary aromatic amines are known as accelerators for unsaturated polyesters.

The principle that aromatic amines may be used as accelerators that, due to their functional groups, react with unsaturated polyesters and thus cannot readily migrate out of the hardened resin, is also known. According to the following references from the literature, accelerators can be incorporated into unsaturated polyesters via primary OH groups by esterification or transesterification: European Patent Application 84,784, U.S. Pat. No. 4,243,763, U.S. Pat. No. 4,284,551, and German Offenlegungsschrift 1,544,698. According to the following references from the literature, accelerators can be incorporated into unsaturated polyesters via epoxide groups by reacting with acid or hydroxyl groups: Belgian Patent 625,701 and British Patent 2,120,653.

As revealed in the comparison examples described below, disadvantages with regard to low reactivity or poor grindability occur during use in surface fillers because they are incorporated, as is documented in European Patent Application 84,784. This also applies to the accelerator according to U.S. Pat. No. 4,297,158, which produces sticky surfaces.

An object of this invention is therefore to provide new accelerators for unsaturated polyester resins that do not have the disadvantages described above, that is, to obtain accelerators that do not migrate out of surface fillers based on unsaturated polyester resins and that ensure good grindability of the hardened surface fillers. This object can be achieved by using the compounds according to the invention, which are described in more detail in the following.

SUMMARY OF THE INVENTION

The present invention relates to compounds of formula (I)

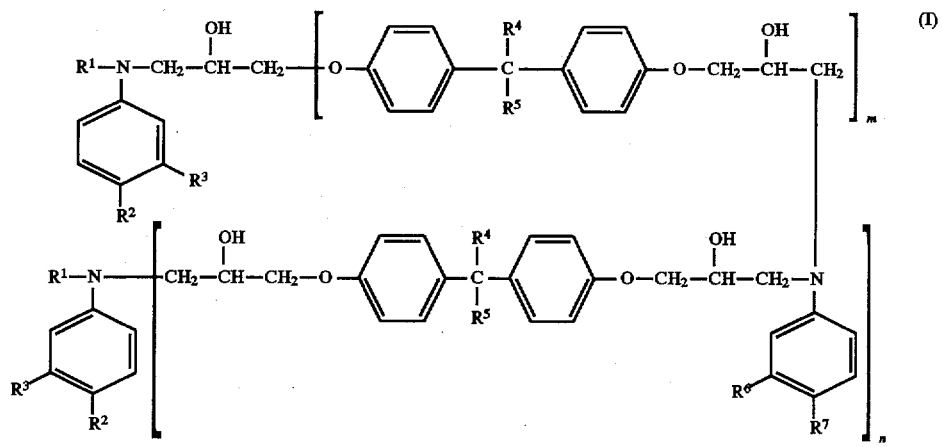

wherein
- $R^1$ represents an alkyl or cycloalkyl group having 1 to 6 carbon atoms, optionally substituted with inert substituents,
- $R^2$ and $R^3$ independently represent hydrogen, alkyl or cycloalkyl groups having 1 to 6 carbon atoms, or halogen atoms,
- $R^4$ and $R^5$ each represent methyl groups or, together with the carbon atom located between the aromatic rings, form a cyclohexane group, optionally substituted with inert substituents,
- $R^6$ and $R^7$ independently represent hydrogen, alkyl or cycloalkyl groups having 1 to 6 carbon atoms, optionally substituted with inert substituents, or halogen atoms,
- m represents an integer or (as a statistical average) a fractional number from 1 to 3, and
- n represents an integer or (as a statistical average) a fractional number from 0 to 2, with the proviso that when m is greater than 1 and n is at least 1, the bracketed segments taken together represent a block copolymer, an alternating copolymer, or a random copolymer, and with the further proviso that if n is 0, then $R^1$ is an ethyl group and either $R^2$ is a methyl group and $R^3$ is hydrogen or $R^2$ is hydrogen and $R^3$ is a methyl group.

The invention also relates to a process for preparing compounds (I) comprising reacting (a) an amine of formula (II)

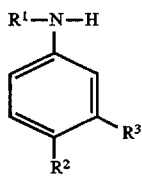

wherein $R^1$ to $R^3$ are defined as above, with (b) a diepoxide of formula (III)

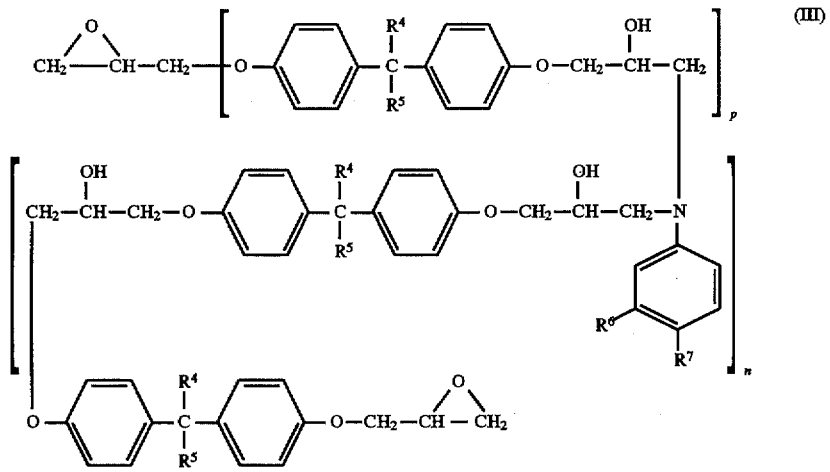

wherein $R^4$ to $R^7$ and n are defined as above for formula (I) and p represents an integer or (as a statistical average) a fractional number from 0 to 2, with the proviso that when n and p are each at least 1, the bracketed segments taken together represent a block copolymer, an alternating copolymer, or a random copolymer, and while maintaining a molar ratio of amine (a) (i.e., component (II)) to epoxide (b) (i.e., component (III)) of about 1.25:1 to about 2:1 within a temperature range of about 100° to about 250° C.

Finally, the invention also relates to the use of the new compounds (I) as hardening accelerators for ethylenically unsaturated, cold hardenable acrylic and polyester resins.

DETAILED DESCRIPTION OF THE INVENTION

Amines of formula (II) that are suitable for performing the process according to the invention are any N-monosubstituted anilines that correspond to formula (II) and to the definitions given above for groups $R^1$ to $R^3$. Among the preferred amines (II) are those in which $R^1$ represents a methyl group or, more preferably, an ethyl group and in which one of each of the groups $R^2$ and $R^3$ represents a methyl group and the other one of each group mentioned represents a hydrogen atom. Examples of suitable amines of formula (II) are N-ethyl-p-toluidine, N-ethyl-m-toluidine, N-ethyl-3-chloro-4-methylaniline, N-ethyl-4-chloro-3-methylaniline, N-ethyl-3,4-dimethylaniline, N-ethyl-p-cyclohexylaniline, N-ethyl-p-t-butylaniline. N-ethyl-p-toluidine and N-ethyl-m-toluidine are particularly preferred.

Diepoxides of formula (III) that are suitable for the process according to the invention include glycidyl ethers of bisphenol A (that is, where n is 0 and $R^4$ and $R^5$ are $CH_3$) having epoxide equivalent weights of 142 to 4000 (preferably 170 to 1000).

Furthermore, diepoxides (III) that are suitable for the process according to the invention are those having incorporated tertiary nitrogen atoms (that is, where n is 1 to 2). Such compounds are reaction products of bisphenol bisglycidyl ethers of the type mentioned above and primary amines of formula (IV)

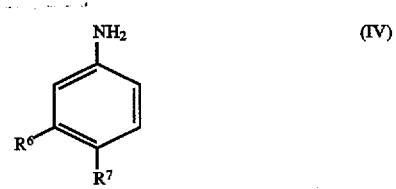

wherein $R^6$ and $R^7$ are defined as above and preferably represent hydrogen or $C_1$–$C_4$ alkyl groups. The preparation of this type of diepoxide with tertiary nitrogen atoms is described, for example, in U.S. Pat. No. 2,819,223.

Regardless of how diepoxides (III) are prepared, the bracketed segments taken together represent a block copolymer, an alternating copolymer, or a random copolymer when n and p are each at least 1. Thus, the bisphenol glycidyl ether epoxide moiety shown outside the brackets of formula (III) is, after reaction with amine (II), shown as an additional bisphenol glycidyl ether group inside the upper bracket of formula (I) (and p of formula (III) increases by 1 to become m in formula (I)). The actual location of the reacted bisphenol glycidyl ether group within a particular molecule, of course, does not change.

Reaction of amines (II) with epoxides (III) takes place within the temperature range 150° to 250° C. (preferably 150° to 210° C., more preferably 180° to 210° C.). The molar ratio of amines of formula (II) to diepoxides of formula (III) is then 1.25:1 to 2:1 (preferably 1.5:1 to 2:1).

According to a preferred embodiment, the process of the invention is performed in such a way that amine (II) is gradually introduced into diepoxide (III) that has been preheated to the reaction temperature, wherein the rate of addition corresponds to the rate of reaction.

The term "inert substituents" as used in the definitions of $R^1$ and $R^4$ to $R^7$ includes groups known in the art, such as $C_1$–$C_6$ alkyl, that do not themselves undergo reactions under the reaction conditions used in the process of the invention.

The reaction according to the invention may be accelerated by oxalkylation catalysts such as tertiary aliphatic amines, phosphines, ammonium and phosphonium salts, alkaline earth and alkali metal hydroxides, salts, and alcoholates.

Compounds of formula (I) according to the invention obtained in this way represent valuable hardening accelerators for unsaturated acrylic resins, particularly polyester resins, and are particularly useful in cold hardening surface fillers based on these resins, particularly those based on unsaturated polyester resins. For this purpose, compounds (I) are preferably used at a concentration corresponding to 0.008 to 0.4 wt. % (preferably 0.04 to 0.2 wt. %) of tertiary amine nitrogen in compounds (I) relative to the resin being hardened.

Compounds of formula (I) according to the invention are generally hard, brittle resins. For improved handling, the resins may be dissolved in suitable solvents or solvent mixtures, preferably during the course of the production process. Preferred solvents of this type are monomers which can be copolymerized with the polyester, such as styrene, α-methyl-styrene, esters of methacrylic acid, and the like. In addition, solvents that are inert to polymerization, such as n-butyl acetate, cyclohexanone, or ethylene glycol dimethyl ether, may also be used to a limited extent, depending on the ultimate application. In this form, the accelerator can easily be metered into the resins at any desired concentration.

Resins that can be hardened using compound (I) according to the invention are in principle all ethylenically unsaturated compounds or mixtures that can be polymerized in the presence of diacyl peroxides but are preferably unsaturated polyester resins and acrylic resins. The term "unsaturated polyester resins" in this sense refers to mixtures of about 30 to about 75 parts by wt. of a α,β-ethylenically unsaturated polyesters and about 70 to about 25 parts by wt. of unsaturated monomers that can be polymerized therewith.

Suitable α,β-unsaturated polyesters of this type include the conventional polycondensation products of at least one α,β-ethylenically unsaturated dicarboxylic acid having, generally, 4 or 5 carbon atoms or their ester-forming derivatives, optionally mixed with up to 90 mol %, relative to the unsaturated acid component, of at least one aliphatic saturated dicarboxylic acid having 4 to 10 carbon atoms or cycloaliphatic, araliphatic, or aromatic dicarboxylic acid having 8 to 10 carbon atoms or their ester-forming derivatives, with at least one polyhydroxyl compound, preferably a dihydroxyl compound with 2 to 8 carbon atoms. Such polyesters are described, for example, in J. R. Lawrence, "Polyester Resins" (Reinbold Publ. Corp., New York 1960), pages 18 et seq., and in Kunststoff-Handbuch, vol. VIII ("Polyesters") (Carl Hanser Verlag, Munich 1973), pages 247–312.

The acid values of the polyesters should be between 1 and 100 (preferably between 55 and 70), the OH values should be between 10 and 150 (preferably between 20 and 100), and the molecular weight $M_n$, measured as a number average, should be between about 500 and about 5000 (preferably between about 1000 and about 3000) (as measured by vapor pressure/osmotic measurements in dioxane and acetone; if the measured values differ, the lower value is regarded as the correct value).

Styrene is the preferred copolymerizable monomer.

The term "acrylic resins" in the sense of the invention refers to polyesters, polyurethanes, polyepoxides, polyols, and polyether polyols that contain (meth)acryloyloxy groups such as described, for example, in German Offenlegungsschriften 2,053,683, 2,261,612, 2,423,354, and 2,838,691 (polyester (meth)acrylates); German Offenlegungsschriften 1,447,929, 1,916,499, and 2,115,373, U.S. Pat. Nos. 2,958, 704 and 3,297,745, and British Patent 743,514 (urethane (meth)acrylates); German Offenlegungsschriften 1,921,869, 2,349,979, 2,411,760, and 2,429,527, British Patents 1,006, 587, and U.S. Pat. Nos. 3,066,112 and 3,804,735 (epoxy (meth)acrylates); German Offenlegungsschrift 1,770,825 and U.S. Pat. Nos. 2,101,107, 2,413,973, 3,368,900, 3,552, 986, and 3,558,387 (polyol (meth)acrylates); and German Offenlegungsschriften 2,651,507 and 2,853,921 and U.S. Pat. Nos. 2,951,758 and 3,380,831 (polyether polyol (meth) acrylates).

In order to lower the viscosity, to increase the reactivity, or to produce special properties, the previously mentioned "acrylic resins" may also be admixed with polymerizable olefinically unsaturated monomers, for example, with (meth)acrylates of monohydric alcohols, hydroxyalkyl (meth)acrylates, (meth)acrylamides, styrene, α-methylstyrene, styrenes ring-substituted by alkyl groups, divinylbenzene, (meth)acrylonitrile, vinyl chloride, vinylidene chloride, vinyl ethers, vinyl acetate, or mixtures thereof. It is, of course, also possible to polymerize at least one α,β-monolefinically unsaturated monomer, such as the type mentioned above, in the presence of compounds (I) according to the invention.

Before the hardening process is carried out, polymerization initiators, preferably diacyl peroxides or percarbonates, are added to the resins in amounts of 1 to 10 wt. % relative to the resin to be polymerized. Preferred initiators include diacetyl peroxide, dibenzoyl peroxide, di-p-chlorobenzoyl peroxide, phthaloyl peroxide, succinyl peroxide, dilauryl peroxide, acetylcyclohexanesulfonyl peroxide, isopropyl percarbonate, cyclohexyl percarbonate, and bis(4-t-butylcyclohexyl) percarbonate.

The resin materials being polymerized may contain conventional fillers, pigments, stabilizers, and disinfectants. When used for dental applications, both organic fillers, such as powdered polyacrylates, and inorganic fillers, such as powdered quartz, glass, silicon dioxide, or aluminum oxide powder, may be considered.

According to the invention, all types of molded items can be cured in the cold and used in a very wide variety of applications in the building and construction industry, in the electrical industry, in the construction of boats, and in the automobile industry.

To prepared preferred surface fillers according to the invention, based on unsaturated polyester resins of the type described by way of example, 50 to 350 parts by wt., relative to 100 parts by wt. of polyester resin, of fillers such as chalk, talc, barite, or aerosil, are added to the polyester resins. Dyes or pigments may, of course, also be added. Mixing the various components in the molding compounds according to the invention is expediently performed in internal mixers, dissolvers, or cylinder mills.

The surface fillers are suitable, for example, for repairing bodywork panels, plastic sheets, and stone slabs of any type. A preferred use according to the invention is for fast setting surface fillers in the automobile repair sector.

The following examples further illustrate details for the preparation and use of the compounds of this invention. The invention, which is set forth in the foregoing disclosure, is not to be limited either in spirit or scope by these examples. Those skilled in the art will readily understand that known variations of the conditions and processes of the following preparative procedures can be used to prepare these compounds. Unless otherwise noted, all temperatures are degrees Celsius and all parts and percentages are parts by weight and percentages by weight, respectively.

EXAMPLES

I. Preparation of Amine Accelerators According to the Invention

Example 1 (accelerator 1)

225 g of a diglycidyl ether of bisphenol A having an epoxide equivalent weight of 500 and molecular weight of 900 were heated to 180° C. in 30 minutes under nitrogen. 64.9 g of N-ethyl-m-toluidine were added dropwise over 4 hours, the temperature was increased to 200° C., and stirring was continued at 200° C. for another 4 hours. After cooling to 110° C., the mixture was adjusted to a solids content of 65% with styrene.

Tertiary amine nitrogen content: 2.52% (relative to 100% resin)

Example 2 (accelerator 2)

200 g of a diglycidyl ether of bisphenol A having an epoxide equivalent weight of 380 and a molecular weight of 770 were heated to 180° C. in 30 minutes under nitrogen. 64.9 g of N-ethyl-m-toluidine were added dropwise over 4 hours, the temperature was increased to 200° C., and stirring was continued at 200° C. for another 4 hours. After cooling to 110° C., the mixture was adjusted to a solids content of 65% with styrene.

Tertiary amine nitrogen content: 2.77% (relative to 100% resin)

Example 3 (accelerator 3)

225 g of a diglycidyl ether of bisphenol A having an epoxide equivalent weight of 500 and a molecular weight of 900 were heated to 180° C. in 30 minutes under nitrogen. 64.9 g of N-ethyl-m-toluidine were added dropwise over 4 hours, the temperature was increased to 200° C., and stirring was continued for another 4 hours at 200° C. After cooling to 110° C., the mixture was adjusted to a solids content of 65% with styrene.

Tertiary amine nitrogen content: 2.39% (relative to 100% resin)

Example 4 (accelerator 4)

180 g of a diglycidyl ether of bisphenol A having an epoxide equivalent weight of 190 and a molecular weight of 380 were heated to 180° C. in 30 minutes under nitrogen. 64.9 g of N-ethyl-m-toluidine were added dropwise over 4 hours, the temperature was increased to 200° C., and stirring was continued for another 4 hours at 200° C. After cooling to 110° C., the mixture was adjusted to a solids content of 65% with styrene.

Tertiary amine nitrogen content: 2.97% (relative to 100% resin).

Example 5 (accelerator 5)

186.5 g of a diglycidyl ether of bisphenol A having an epoxide equivalent weight of 190 and a molecular weight of 400 were heated to 160° C. in 30 minutes under nitrogen. 23.25 g of aniline were added dropwise over 4 hours, 67.5 g of N-ethyl-m-toluidine were then added dropwise over 2 hours at 160° C., and stirring was continued for another 2 hours at 160° C. After cooling to 110° C., the mixture was adjusted to a solids content of 65% with styrene.

Tertiary amine nitrogen content: 4.26% to 4.28% (relative to 100% resin).

Example 6 (accelerator 6)

186.5 g of a diglycidyl ether of bisphenol A having an epoxide equivalent weight of 190 and a molecular weight of 400 were heated to 160° C. in 30 minutes under nitrogen. 26.75 g of m-toluidine were added dropwise over 4 hours, 67.5 g of N-ethyl-m-toluidine were then added dropwise over 2 hours at 160° C., and stirring was continued for another 2 hours at 160° C. After cooling to 110° C., the mixture was adjusted to a solids content of 65% with styrene.

Tertiary amine nitrogen content: 3.95% to 3.98% (relative to 100% resin).

II. Preparation of Comparison Amine Accelerators

Comparison Example 1 (accelerator according to European Patent Application 84,784)

214 g of m-toluidine were heated to 195° C. under $N_2$ and 400 g of a diglycidyl ether of bisphenol A (epoxide equivalent 190, molecular weight 380) were added dropwise over 5 hours with stirring. After stirring for a further 5 hours at 180° to 200° C., the mixture was cooled to 150° C. 86 g of ethylene oxide were then introduced over the course of 10 hours. A brittle resin was produced.

Tertiary amine nitrogen content: 3.8%

Comparison Example 2 (accelerator according to Belgian Patent 625,701)

1 mole of N,N-bisglycidyl-m-toluidine was prepared from 4.8 moles of m-toluidine and 2 moles of epichlorohydrin. The excess m-toluidine was required to produce the oxirane ring and was filtered off as the hydrochloride after completion of the reaction.

Tertiary amine nitrogen content: 6.3%

Comparison Example 3 (accelerator according to British Patent 2,120,653)

71.3 g of p-toluidine (0.67 mol) were initially placed under $N_2$ in a 250 ml reaction vessel and heated to 160° C. 180 g of a bisphenol A diglycidyl ether having a molecular weight of 380 was added over the course of 15 minutes, without further heating, in such a way that the reaction temperature did not exceed 170° C. 50 g of phenylglycidyl ether (0.33 mol) was then added over 10 minutes and the temperature was held at 170° C. for 60 minutes.

Tertiary amine nitrogen content: 3%

Comparison Example 4 (accelerator according to U.S. Pat. No. 4,243,763)

A polymeric amine with 1 to 8 amine units was prepared by adding 380 g of the diglycidyl ether of bisphenol A to n-butyl-p-aminophenyl acetate. This product was then allowed to react with excess methacrylic acid (2.5 mol) in the presence of butylhydroxytoluene to give a condensation product.

Tertiary amine nitrogen content: 1.8%

Comparison Example 5 (accelerator according to U.S. Pat. No. 4,297,158)

107 g of N-methylaniline and 500 g of the diglycidyl ether of bisphenol A in accordance with Example 1 were placed under $N_2$ in a one-liter flask having a stirrer, reflux condenser, and thermometer. After adding 100 ppm of hydroquinone, the mixture was heated to 100° C. for 24 hours.

Tertiary amine nitrogen content: 2.3%

Comparison Example 6 (accelerator according to U.S. Pat. No. 4,284,551)

1 mole of p-aminophenylethanol was allowed to react under $N_2$ with 2 moles of a bisglycidyl ether of bisphenol A (molecular weight 380, epoxide equivalent weight 180 g/equiv) for 4 hours at 170° C., and the reaction product was then allowed to react with 2 moles of N-ethyl-p-aminophenylethanol over 2 hours at 170° C. to give the comparison accelerator.

Tertiary amine nitrogen: 3.4%

Comparison Example 7 (accelerator according to German Offenlegungsschrift 1,544,698)

30.2 g of (N-β-hydroxyethyl)-p-toluidine, 19.7 g of ethylene bromide, and 16.8 g of sodium bicarbonate were heated under reflux in 100 ml of water for 40 hours. The organic phase was separated off, residues of starting material were removed under vacuum, and the product was precipitated twice from ethanol containing water. 19 g of 1,2-bis[(N-β-hydroxyethyl)-p-toluidino]ethane were obtained.

Tertiary amine nitrogen content: 8%

III. Preparation of an Unsaturated Polyester Resin

A polyester was prepared by melt condensation from 479 g (4.52 mol) of diethylene glycol and 421 g (4.3 mol) of maleic anhydride. 177 g (1.34 mol) of dicyclopentadiene were added at the same time. The resin was dissolved in styrene to give a 65% strength solution and stabilized with 0.02% toluhydroquinone. The resultant polyester resin had a viscosity of 500 to 650 mPa·s (measured at 23° C.) and an acid value of 10.

IV. Determination of Reactivities

Cold-hardening casting compounds were prepared from the polyester resin using the previously mentioned accelerators. The amounts of amine nitrogen provided at the stated concentrations in the cold-hardening resin enabled a comparison of the reactivities of the individual accelerators. The reactivity was determined by curing the accelerator/resin mixture at an initial temperature of 25° C. using 2% commercially available benzoyl peroxide paste (50% benzoyl peroxide content).

The gel time, hardening time, and maximum temperature were determined in accordance with DIN 16,945.

Amine accelerators according to the invention

The accelerators according to the invention were used as 65% strength solutions in styrene.

| | Example | | | | | |
|---|---|---|---|---|---|---|
| | 1 | 2 | 3 | 4 | 5 | 6 |
| Accelerator added (%) | 7.4 | 8.15 | 7.7 | 6.22 | 4.3 | 4.7 |
| Total N (%) | 0.12 | 0.146 | 0.12 | 0.12 | 0.12 | 0.12 |
| Gel time (min) | 6.2 | 5.3 | 6.2 | 5.8 | 9.4 | 6.9 |
| Hardening time (min) | 8.2 | 7.5 | 8.5 | 8.1 | 13.1 | 9.2 |
| T max (°C.) | 94 | 98 | 94 | 98 | 90 | 97 |

Comparison amine accelerators

The comparison amine accelerators were used as 65% strength solutions in styrene.

| | Comparison Example | | | | | | |
|---|---|---|---|---|---|---|---|
| | 1 | 2 | 3 | 4 | 5 | 6 | 7 |
| Accelerator added (%) | 5.0 | 3 | 6 | 10.3 | 8 | 5.5 | 2.3 |
| Total N (%) | 0.12 | 0.12 | 0.12 | 0.12 | 0.12 | 0.12 | 0.12 |
| Gel time (min) | 7.3 | 10.1 | 8.3 | 13.3 | 9.4 | 8.7 | 1.3 |
| Hardening time (min) | 9.4 | 14 | 10.7 | 17.2 | 14.6 | 12.3 | 2.4 |
| T max (°C.) | 90 | 85 | 91 | 86 | 83 | 90 | 91 |

V. Preparation of Surface Fillers 100 parts of polyester resin were homogenized each time with the relevant accelerator, 130 parts of talc, 60 parts of barite, and 7 parts of titanium dioxide (rutile).

100 g of surface filler were stirred up with about 2 g of a commercially available 50% strength benzoyl peroxide paste. The materials were then applied at a thickness of about 1 mm to degreased and ground steel plates. The grindability was determined after specific times.

| Compositions of surface fillers according to the invention | | | | | | |
|---|---|---|---|---|---|---|
| | Surface filler | | | | | |
| | A | B | C | D | E | F |
| Polyester resin added (parts) | 100 | 100 | 100 | 100 | 100 | 100 |
| Accelerator | 1 | 2 | 3 | 4 | 5 | 6 |
| Amount added (parts) | 7.4 | 8.15 | 7.7 | 6.22 | 4.3 | 4.7 |
| Filler (parts) | 197 | 197 | 197 | 197 | 197 | 197 |

| Compositions of comparison surface fillers | | | | | | | |
|---|---|---|---|---|---|---|---|
| | Surface filler | | | | | | |
| | H | I | J | K | L | M | N |
| Polyester resin added (parts) | 100 | 100 | 100 | 100 | 100 | 100 | 100 |
| Comparison example | 1 | 2 | 3 | 4 | 5 | 6 | 7 |
| Amount added (parts) | 5.0 | 3.0 | 6.0 | 10.3 | 8.0 | 5.5 | 2.3 |
| Filler (parts) | 197 | 197 | 197 | 197 | 197 | 197 | 197 |

VI. Determination of Grindability

The grindability was assessed at various times after adding the peroxide by grinding the cured surface filler with sandpaper of average coarseness (80 paper) by hand by the same person. Both the amount of filler removed and the degree of clogging on the sandpaper were assessed using the following scales.

Behavior of the filler when ground:

1 very easily ground down
2 easily ground down
3 moderately ground down
4 poorly ground down
5 very poorly ground down Behavior of sandpaper during grinding:

a no clogging
b some clogging
c somewhat more clogging
d considerable clogging
e filled in while grinding

| Grindability of surface fillers with accelerators according to the invention | | | | | | |
|---|---|---|---|---|---|---|
| Surface filler | A | B | C | D | E | F |
| Accelerator (Ex.) | 1 | 2 | 3 | 4 | 5 | 6 |
| Shore D | | | | | | |
| 12 min | 36 | 35 | — | 39 | — | — |
| 1 hr | 77 | 77 | 5 | 77 | 70 | 75 |
| Grindability | | | | | | |
| 12 min | 1-2c-d | 1-2b-c | 2d | 1-2a | 2d | 2d |
| 15 min | 1-2b | 1-2a | 1-2a-b | 1-2a | 2c | 1-2c |
| 20 min | 1-2a | 1-2a | 1-2a | 1-2a | 1b | 1-2a |

| Grindability of comparison surface fillers | | | | | | |
|---|---|---|---|---|---|---|
| Surface filler | H | I | J | K | L | M | N |
| Comp. accelerator (Comp. Ex.) | 1 | 2 | 3 | 4 | 5 | 6 | 7 |
| Shore D | | | | | | | |
| 12 min | 32 | — | 34 | — | — | 32 | 35 |
| 1 hr | 68 | 60 | 70 | 65 | 60 | 71 | 73 |
| Grindability | | | | | | | |
| 12 min | — | — | 3d | — | — | 3d | 4b |
| 15 min | 2c | 2d | 2c | 3d | — | 3c | 4c |
| 20 min | 2b | 2c | 2b | 2c | 4d | 2b | 3c |

What is claimed is:

1. A compound having the formula

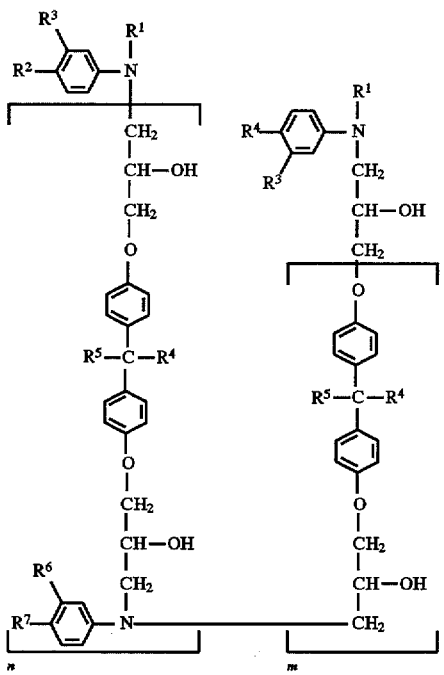

wherein $R^1$ represents an alkyl or cycloalkyl group having 1 to 6 carbon atoms, optionally substituted with inert substituents, $R^2$ and $R^3$ independently represent hydrogen, alkyl or cycloalkyl groups having 1 to 6 carbon atoms, or halogen atoms, $R^4$ and $R^5$ each represent methyl groups or, together with the carbon atom located between the aromatic rings, form a cyclohexane group, optionally substituted with inert substituents, $R^6$ and $R^7$ independently, represent hydrogen, alkyl or cycloalkyl groups having 1 to 6 carbon atoms, optionally substituted with inert substituents, or halogen atoms, m represents an integer or (as a statistical average) a fractional number from 1 to 3, and n represents an integer or (as a statistical average) a fractional number from 0 to 2, with the proviso that when m is greater than 1 and n is at least 1, the bracketed segments taken together represent a block copolymer, an alternating copolymer, or a random copolymer, and with the further proviso that if n is 0, then $R^1$ is an ethyl group and either $R^2$ is a methyl group and $R^3$ is hydrogen or $R^2$ is hydrogen and $R^3$ is a methyl group.

2. A compound according to claim 1 wherein either $R^2$ is a methyl group and $R^3$ is hydrogen or $R^2$ is hydrogen and $R^3$ is a methyl group.

3. A compound according to claim 1 wherein $R^1$ is a methyl or ethyl group.

4. A method for hardening ethylenically unsaturated cold hardenable acrylic and polyester resins in the presence of a hardening accelerator comprising adding to said resins a hardening accelerator comprising a compound according to claim 1.

* * * * *